United States Patent [19]
Raskin

[11] Patent Number: 6,096,546
[45] Date of Patent: Aug. 1, 2000

[54] METHODS FOR RECOVERING POLYPEPTIDES FROM PLANTS AND PORTIONS THEREOF

[75] Inventor: Ilya Raskin, Manalapan, N.J.

[73] Assignee: Board of Trustees, Rutgers, The State University of New Jersey

[21] Appl. No.: 09/015,605

[22] Filed: Jan. 30, 1998

[51] Int. Cl.$^7$ ....................................................... C12N 5/00
[52] U.S. Cl. ........................ 435/410; 210/600; 435/68.1; 435/69.1; 435/70.1
[58] Field of Search .................................... 435/410, 68.1, 435/69.1, 70.1; 47/58.1; 210/600

[56] References Cited

U.S. PATENT DOCUMENTS 5,650,307  7/1997  Sijmons .

FOREIGN PATENT DOCUMENTS

| | | |
|---|---|---|
| 0598589 | 5/1994 | European Pat. Off. . |
| WO 84/02920 | 8/1984 | WIPO . |
| WO 91/02066 | 2/1991 | WIPO . |
| WO 92/22582 | 12/1992 | WIPO . |
| WO 95/14099 | 5/1995 | WIPO . |
| WO 96/04392 | 2/1996 | WIPO . |
| WO 97/04122 | 2/1997 | WIPO . |
| WO 97/10353 | 3/1997 | WIPO . |

OTHER PUBLICATIONS

Magwa, M.L., et al., "Guttation Fluid Peroxidases from Helianthus Annus," *Phytochemistry*, 32:251–253 (1993).
Verwoerd, T. C. et al., "Stable Accumulation of Aspergillus Niger Phytase in Transgenic Tobacco Leaves" *Plant Physiology*, 109:1199–1205 (1995).
International Search Report (International Application No. PCT/US99/02071).
Ahmed, A.E. et al., "Cell Wall Metabolism in Ripening Fruit II. Changes in Carbohydrate–Degrading Enzymes in Ripening Bartlett Pears," *Plant Physiol.*, 65:1014–1016 (1980).
Bichko, V. et al., "Subtype ayw variant of hepatitis B virus" *FEBS 2617*, 185(1):208–212 (Jun. 1985).
Biely, P. et al., "Remazol Brilliant Blue–Xylan: A Soluble Chromogenic Substrate for Xylanases," *Meth. Enzymol.*, 160:536–541 (1988).
Chomczynski, P. et al., "Single–Step Method of RNA Isolation by Acid Guanidinium Thiocyanate–Phenol–Chloroform Extraction," *Analytical Biochemistry*, 162:156–159 (1987).
Christou, P., "Strategies for variety–independent genetic transformation of important cereals, legumes and woody species utilizing particle bombardment," *Euphytica*, 85:13–27 (1995).
Cullen, B.R. et al., "Secreted Placental Alkaline Phosphatase as a Eukaryotic Reporter Gene," *Meth. Enzymol.*, 216:362–368 (1992).
Dibner, M.D., "Biotechnology and Pharmaceuticals 10 Years Later," *BioPharm*, 10(9): 24–30 (Sep. 1997).
Esaka, M. et al., "Secretion of basic and acidic chitinases from salt–adapted and—unadapted winged bean cells," *Physiologia Plantarum*, 92:90–96 (1994).

Esaka, M. et al., H., "Specific Secretion of Proline–Rich Proteins by Salt–Adapted Winged Bean Cells," *Plant Cell Physiol.*, 36(3):441–446 (1995).
Esaka, M. et al., "Stimulation of Ascorbate Oxidase Secretion From Cultured Pumpkin Cells by Divalent Cations," *Phytochemistry*, 28(10):2655–2658 (1989).
Goddijn, O.J.M. et al., "Plants as bioreactors," *Tibtech*, 13:379–387 (Sep. 1995).
Grépinet, O. et al., "Nucleotide Sequence and Deletion Analysis of Xylanase Gene (xynZ) of *Clostridium thermocellum*," *J. Bacteriol.*, 170(10):4582–4588 (Oct. 1988).
Heim, R. et al., "Improved green fluorescence," *Nature*, 373:663–664 (Feb. 23, 1995).
Herbers, K. et al., "A Thermostable Xylanase from *Clostridium thermocellum* Expressed at High Levels in the Apoplast of Transgenic Tobacco Has No Detrimental Effects and Is Easily Purified," *Bio/Technology*, 13:63–66 (Jan. 13, 1995).
Hood, E.E. et al., "The Hypervirulence of *Agrobacterium tumefaciens* A281 Is Encoded in a Region of pTiBo542 Outside of T–DNA," *J. Bacteriol.*, 168(3): 1291–1301 (Dec. 1986).
Jähne, A. et al., "Genetic engineering of cereal crop plants: a review," *Euphytica*, 85:35–44 (1995).
Li, J. et al., "Secretion of Active Recombinant Phytase from Soybean Cell–Suspension Cultrues," *Plant Physiol.*, 114:1103–1111 (1997).
Ma, J. K–C. et al., "Assembly of monoclonal antibodies with IgG1 and IgA heavy chain domains in transgenic tobacco plants," *Eur. J. Immunol.*, 24:131–138 (1994).
Margulies, M.M., "Effects of Chloramphenicol on Light Dependent Development of Seedlings of *Phaseolus vulgaris* var. Black Valentine, With Particular Reference to Development of Photosynthetic Activity," *Plant Physiol.*, 15: 473–480 (1962).
Mehta, A. et al., "Hepatitis B virus (HBV) envelope glycoproteins vary drastically in their sensitivity to glycan processing: Evidence that alteration of a single N–linked glycosylation site can regulate HBV secretion," *Proc. Natl. Acad. Sci., USA*, 94:1822–1827 (Mar. 1997).
Miele, L. "Plants as bioreactors for biopharmaceuticals: regulatory considerations," *Tibtech*, 15(2):45–50 (Feb. 1997).

(List continued on next page.)

*Primary Examiner*—Leon B. Lankford, Jr.
*Attorney, Agent, or Firm*—Marshall, O'Toole, Gerstein, Murray & Borun

[57] ABSTRACT

Methods for using plants or intact portions thereof to produce and exude heterologous polypeptides are disclosed. The methods of the invention use whole plants or portions thereof that are intact, living and capable of exuding the produced polypeptides. The methods of the invention minimize operator intervention and exploit solar energy and the minimal nutrient needs of photoautotrophic organisms to provide inexpensive and indefinitely sustainable methods for producing a variety of heterologous polypeptides.

11 Claims, 6 Drawing Sheets

OTHER PUBLICATIONS

Ni, M. et al., "Sequence–specific interactions of wound–inducible nuclear factors with mannopine synthase 2' promoter wound–responsive elements," *Plant. Mol. Biol.*, 30:77–96 (1996).

Parent, J–G et al., "Detection of pathogenesis–related proteins (PR or b) and of other proteins in the intercellular fluid of hypersensitive plants infected with tobacco mosaic virus," *Can. J. Bot.*, 62:564–569 (1984).

Pen, J. et al., "Phytase–containing Transgenic Seeds as a Novel Feed Additive for Improved Phosphorus Utilization," *Bio/Technology*, 11:811–814 (Jul. 1993).

Pen, J. et al., "Production of Active *Bacillus Licheniformis* Alpha–Amylase in Tobacco and its Application in Starch Liquefaction," *Bio/Technology*, 10:292–296 (Mar. 1992).

Priya Sethu, K.M. et al., "Post–Harvest Biochemical Changes Associated with the Softening Phenomenon in *Capsicum Annuum* Fruits," *Phytochemistry*, 42(4):961–966 (1996).

Reichel, C. et al., "Enhanced green fluorescence by the expression of an *Aequorea victoria* green fluorescent protein mutant in mono– and dicotyledonous plant cells," *Proc. Natl. Acad. Sci., USA*, 93:5888–5893 (Jun. 1996).

Sijmons, P.C. et al., "Production of Correctly Processed Human Serum Albumin in Transgenic Plants," *Bio/Technology*, 8:217–221 (Mar. 1990).

von Schaewen, A. et al., "Expression of a yeast–derived invertase in the cell wall of tobacco and Arabidopsis plants leads to accumulation of carbohydrate and inhibition of photosynthesis and strongly influences growth and phenotype of transgenic tobacco plants," *EMBO J*, 9(10):3033–3044 (1990).

Wahl, M.F. et al., "Effects of Dimethyl Sulfoxide on Heavy Chain Monoclonal Antibody Production from Plant Cell Culture," *Biotechnology Letters*, 17(5):463–468 (1995).

Wongsamuth, R. et al., "Production of Monoclonal Antibodies by Tobacco Hairy Roots," *Biotechnology & Bioengineering*, 54(5):401–415 (Jun. 5, 1997).

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 33 base pairs
      (B) TYPE: nucleic acid
      (C) STRANDEDNESS: single
      (D) TOPOLOGY: linear    (ii) MOLECULE TYPE: cDNA    (xi) SEQUENCE DESCRIPTION: SEQ ID NO:1:

GGTTCGAATT CGATCTCACA ACAGTGGGCA TGG                    33

(2) INFORMATION FOR SEQ ID NO:2:

(i) SEQUENCE CHARACTERISTICS:
      (A) LENGTH: 34 base pairs
      (B) TYPE: nucleic acid
      (C) STRANDEDNESS: single
      (D) TOPOLOGY: linear

```
        (ii) MOLECULE TYPE: cDNA (xi) SEQUENCE DESCRIPTION: SEQ ID NO:2:

CTCTTTAAAC CATGGAGACC TCAGCGGAGA CGAC                                       34

(2) INFORMATION FOR SEQ ID NO:3:

(i) SEQUENCE CHARACTERISTICS:
           (A) LENGTH: 17 amino acids
           (B) TYPE: amino acid
           (C) STRANDEDNESS: Not Relevant
           (D) TOPOLOGY: Not Relevant (ii) MOLECULE TYPE: peptide (xi) SEQUENCE DESCRIPTION: SEQ ID NO:3:

Met Leu Leu Leu Leu Leu Leu Leu Gly Leu Arg Leu Gln Leu Ser Leu
1               5                   10                  15

Gly
```

METHODS FOR RECOVERING POLYPEPTIDES FROM PLANTS AND PORTIONS THEREOF

FIELD OF THE INVENTION

The present invention relates to processes for recovering products from plants. In particular, the invention relates to processes for expressing and recovering heterologous polypeptides from plants and intact portions thereof

BACKGROUND OF THE INVENTION

Biological methods for the production of chemicals have shown promise as alternatives to traditional chemical syntheses, particularly for complex biochemicals such as polypeptides and proteins. The full potential of these biological methods, which rely on self-reproducing life forms as chemical producers, has not yet been realized, however. Although several biological systems have been successfully explored as potential sources of a variety of chemicals, each system has been found to have its limitations.

The simplest and most thoroughly investigated biological methods for chemical production are microbiological systems. Primitive prokaryotic cells have been amenable to investigation and have been found to produce a variety of small organic and inorganic compounds, as well as a variety of complex biomolecules, such as homologous and heterologous polypeptides and proteins. The most extensively characterized prokaryote, *Escherichia coli,* synthesizes complex biomolecules using a relatively straightforward process of gene expression requiring minimal expression control elements and an uninterrupted coding region. Further, genetic elements encoding heterologous polypeptides can be introduced and expressed in *E. coli* without much difficulty. With these advantages, a wide variety of polypeptides have been expressed in a controlled manner in this organism. However, *E. coli* cultures do require the costly inputs of energy and nutrients. The organism also does not readily secrete the produced polypeptides, adding to the time and expense required to isolate the desired compound. Although other microbes, e.g., species of Bacillus, do secrete polypeptides into growth media, cultures of these organisms also require costly inputs of energy and nutrients. Moreover, all of these primitive prokaryotic systems exhibit additional shortcomings such as the expensive effort to avoid culture contamination and the inability of the microbes to properly process or derivatize many expressed polypeptides to fully biologically active forms.

Yeast, a fairly primitive eukaryotic cell, has also been used to produce chemicals, including heterologous polypeptides. Although these cells may do a better job of reproducing the natural derivatization of most commercially desirable (i.e., eukaryotic) polypeptides, the reproduction is imperfect. Additionally, cultures of yeast cells are also susceptible to contamination and the cells themselves require valuable resources in the forms of energy and nutrients, Efforts to obtain the desired chemicals, such as heterologous polypeptides, are also burdened by the frequent need to extract the chemical from the cell and purify that compound from the chemically complex contents of the yeast cell released during extraction.

Plant cells also reportedly produce chemicals such as native and heterologous polypeptides. Existing genetic transformation technologies allow the transfer of genes into a wide variety of plant cell lines. In addition, a number of regulatory elements and signal sequences have been found that facilitate the expression of heterologous gene products in plant cells. Further, plant cell cultures have been shown to secrete low levels of heterologous proteins. Pen et al., Bio/Technology 10:292–296 (1992) reported that a bacterial signal sequence for alpha-amylase would direct secretion of this protein from tobacco cells. Thus, the plant cell wall has been shown to be permeable to polypeptides as large as 150 kDa. These tools have been used to reportedly engineer plant cells to produce and secrete a variety of heterologous polypeptides, as noted by Esaka et al., Phytochem. 28:2655–2658 (1989), Esaka et al., Physiologia Plantarum 92:90–96 (1994), Esaka et al., Plant Cell Physiol. 36:441–446 (1995), and Li et al., Plant Physiol. 114:1103–1111 (1997). Other polypeptides produced in plant cells include the Hepatitis B surface antigen (HBsAg), the enterotoxin B (LT-B) subunit from *E. coli* (a diarrhea inducer), a variety of antibodies, human growth factors, and hormones. Although these cells secrete the desired polypeptides, these systems also require energy and nutrient inputs that add to the costs of polypeptide recovery.

Mammalian cells, although expected to closely approximate the native derivation of many important polypeptides (e.g., human polypeptides), are very costly to culture, due to their sensitivity to contaminants, their requirements for energy, gases, and nutrients, and their limited lifespans. Isolation of the produced chemicals also would be relatively expensive in view of the typical inability of mammalian cells to secrete products and the relative chemical complexity of the intracellular environment of these cells.

More complex life forms, such as tissues, have not been shown to be practical sources of chemicals such as heterologous polypeptides. In brief, tissue culture suffers from the disadvantages noted above in the context of discussing cell culture. Similarly, organ culture has not been a focus of chemical production on a commercial scale. In general, the cells, tissues, and organs of a multi-cellular organism require costly intervention to ensure their survival and productivity.

Organisms have also been recruited to produce desirable chemicals, including heterologous polypeptides expressed from transgenes. Organism-based methods are freed from some of the restrictions limiting the aforementioned methods. For example, a relatively limited set of chemical inputs can be converted by the synthetic capacity of an organism into the full set of chemicals required to live and grow. Perhaps for this reason, organism-based methods appear to be hardier than cell-, tissue-, or organ-based methods for chemical production. Nevertheless, organisms, particularly heterotrophic organisms such as animals, do require chemical inputs to provide sources of energy and essential nutrients. Frequently, efforts must also be made to ward off disease resulting from, e.g., infection.

Plants, as photoautotrophic organisms, provide an alternative to heterotrophic animals as life forms for the production of chemicals. Transgenic plants have been generated, albeit typically to improve the characteristics of the plants themselves (e.g., to confer resistance to disease, to improve the yield of edible foodstuffs). Nevertheless, some transgenic plants have been used to produce chemicals such as heterologous polypeptides. As noted above, a variety of expression control sequences (e.g., regulatory elements, signal peptide sequences) have been found to function in plant cells generally, or to preferentially function in the cells of particular plant tissues and organs. For example, Sijimons et al. (U.S. Pat. No. 5,650,307) expressed Human Serum Albumin (HSA) by fusing the HSA coding region to the leader sequence from Alfalfa Mosaic Virus. This fused coding region was placed under the control of the Cauliflower Mosaic Virus 35S promoter and the Nopaline Synthase terminator. The HSA was expressed in transgenic potato plants and transgenic tobacco cells. Sijmons et al. further disclosed the secretion of HSA by potato plant cells and recovery of the heterologous HSA from the intercellular space of those plants. Of course, this recovery method involved the destruction of the potato plants.

U.S. Pat. No. 5,580,768 also discloses the production and secretion of heterologous protein by a plant. In particular, the '768 Patent discloses a transgenic rubber tree, with the expressed transgene protein being collected from wounds as a part of the latex. This system is highly specialized for use with Hevaea species (perennial tree species with slow growth), and the tree must be damaged by wounding to recover the heterologous polypeptide in the form of a latex mixture.

Transformed plant material has also been used to express heterologous polypeptides. Wongsamuth et al., Biotech. and Bioengineer. 54:401–415 (1997), report the use of hairy root cultures to express murine $IgG_1$ monoclonal antibody. Further, some antibody activity was found in the medium of the hairy root cultures maintained under axenic conditions as heterotrophic biomasses requiring costly energy and nutrient inputs.

Thus, a need continues to exist in the art for biological methods for economically producing and recovering a wide variety of chemicals, including heterologous polypeptides, in quantity and without destruction of the biological producer.

SUMMARY OF THE INVENTION

The present invention satisfies the aforementioned need in the art by providing for efficient recovery of polypeptide products from exudates of plants or plant portions that synthesize and exude the desired product into the surrounding medium. As photosynthetic organisms, plants are able to utilize free solar energy for growth and production of the desired chemicals. As autotrophs, the plants synthesize many of the biochemicals required for growth and chemical production, rather than requiring costly external sources for these compounds. In addition to low cost, the methods of the invention offer advantages arising from their simplicity and versatility. For example, in the production of heterologous polypeptides, operator intervention is limited to introducing an expressible recombinant coding region into a plant or plant portion, establishing the minimal conditions required for viability and expression, and collecting the expressed polypeptide following its exudation from the plant or plant portion. As such, the processes of the present invention are distinctly advantageous in comparison to prior methods requiring the wounding of plants or the maintenance of plant biomasses. The methods are versatile in being adaptable to a variety of production systems such as soil-based, aqueous fluid-based (hydroponics), and inert substrate-based (aeroponics) environments that are open or closed and containerized or unbounded. The versatility of the methods of the invention is also apparent in the wide variety of plants that may be used and the range of chemicals that may be produced.

One aspect of the invention thus provides improvements in processes for recovery of a heterologous polypeptides from a plant having cells genetically transformed to express and secrete a heterologous polypeptide, wherein the improvements comprise externally contacting the plant, or an intact portion thereof wherein expression occurs, with an aqueous medium to effect an admixture of said medium and plant exudate, and recovering the polypeptide from the admixture.

Preferred for use in the processes of the present invention are intact plants. A wide variety of floating, submerged, and soil-based plants are useful in the inventive methods, including monocots such as ryegrass, alfalfa, turfgrass, eelgrass, duckweed, and wilgeon grass as well as dicots such as tobacco, tomato, rapeseed, Azolla, floating rice, water hyacinth and any of the flowering plants. Additional plants capable of recombinant polypeptide expression and exudation also may be used in the methods of the invention. The contacting step of the inventive processes may involve a culture system relying on soil-based cultivation or water-based cultivation such as hydroponics or aeroponics. The recombinant polypeptide is recovered from exudate, which may be root exudate, guttation fluid oozing from the plant as an exudate via leaf hydathodes, or other sources of exudate, regardless of xylem pressure. The contacting and recovering steps of the processes may be performed continuously or in a batch mode.

In another aspect of the invention, the improvement comprises using a portion of a plant in processes for recovering a polypeptide. The plant portions for use in the processes of the invention are intact and living plant structures. These plant portions may be distinct plant structures, e.g., shoots, leaves, and roots. Alternatively, plant portions may be part or all of a plant organ or tissue, provided the material is intact and alive.

In yet another aspect of the invention, the invention comprises recovering a polypeptide directly from a collected exudate, preferably guttation fluid, of a plant or a portion thereof The recovery may be continuous.

Numerous other aspects and advantages of the present invention will be apparent upon consideration of the following detailed description, reference being made to the drawing wherein:

DETAILED DESCRIPTION OF THE INVENTION

The present invention is versatile in providing methods readily adaptable to the production and recovery of a variety of heterologous polypeptides. A polypeptide is herein defined to include peptides of any length or sequence, and may be derivatized in any manner known in the art. Further, the definition of a polypeptide used herein extends to proteins and their fragments, whether single or multiple chain, and derivatized or not. These polypeptides are encoded by nucleic acids, which can be joined to a variety of expression control elements, including tissue-specific plant promoters, enhancers, secretory signal sequences and terminators. These expression control sequences, in addition to being adaptable to the expression of a variety of gene products, afford a level of control over the timing and extent of production. By concentrating this production in the cells of intact plants and portions thereof, the invention eliminates costly requirements for energy, nutrients, and asepsis during production.

The produced and extracelluarly secreted polypeptides are recovered from plant exudate. The term "exudate" is given its ordinary meaning of that which oozes out. In the context of plant biology, as applied herein, an "exudate" is a fluid that is or has, exited or oozed out of a plant or portion thereof, frequently as a result of xylem pressure, diffusion, or facilitated transport (i.e., secretion). Thus, the invention also minimizes costly post-production manipulations to isolate the produced chemicals. Further, the invention provides these benefits within the context of a system that is indefinitely sustainable.

The following examples illustrate presently preferred embodiments of the invention. Example 1 describes the construction of recombinant polynucleotides for expression of heterologous polypeptides in plants. Example 2 discloses the generation of transgenic plants by transformation with the recombinant polynucleotides. Examples 3–6 illustrate the production, secretion/exudation, and recovery of Xylanase (a prokaryotic enzyme), human placental SEcreted Alkaline Phosphatase (SEAP), Green Fluorescent Protein (GFP, a eukaryotic protein), and Hepatitis B surface Antigen (HbsAg), respectively, using transgenic tobacco plants. Example 7 shows the production, secretion/exudation, and recovery of heterologous polypeptides using transgenic tomato plants (i.e., dicots). Example 8 provides a description of the production, secretion/exudation, and recovery of heterologous polypeptides using transgenic turfgrass (i.e., a monocot). Example 9 illustrates the recovery of heterologous polypeptide from an exudate in the form of guttation fluid, using a soil-based cultivation system.

EXAMPLE 1

Polynucleotides

Figure 1:
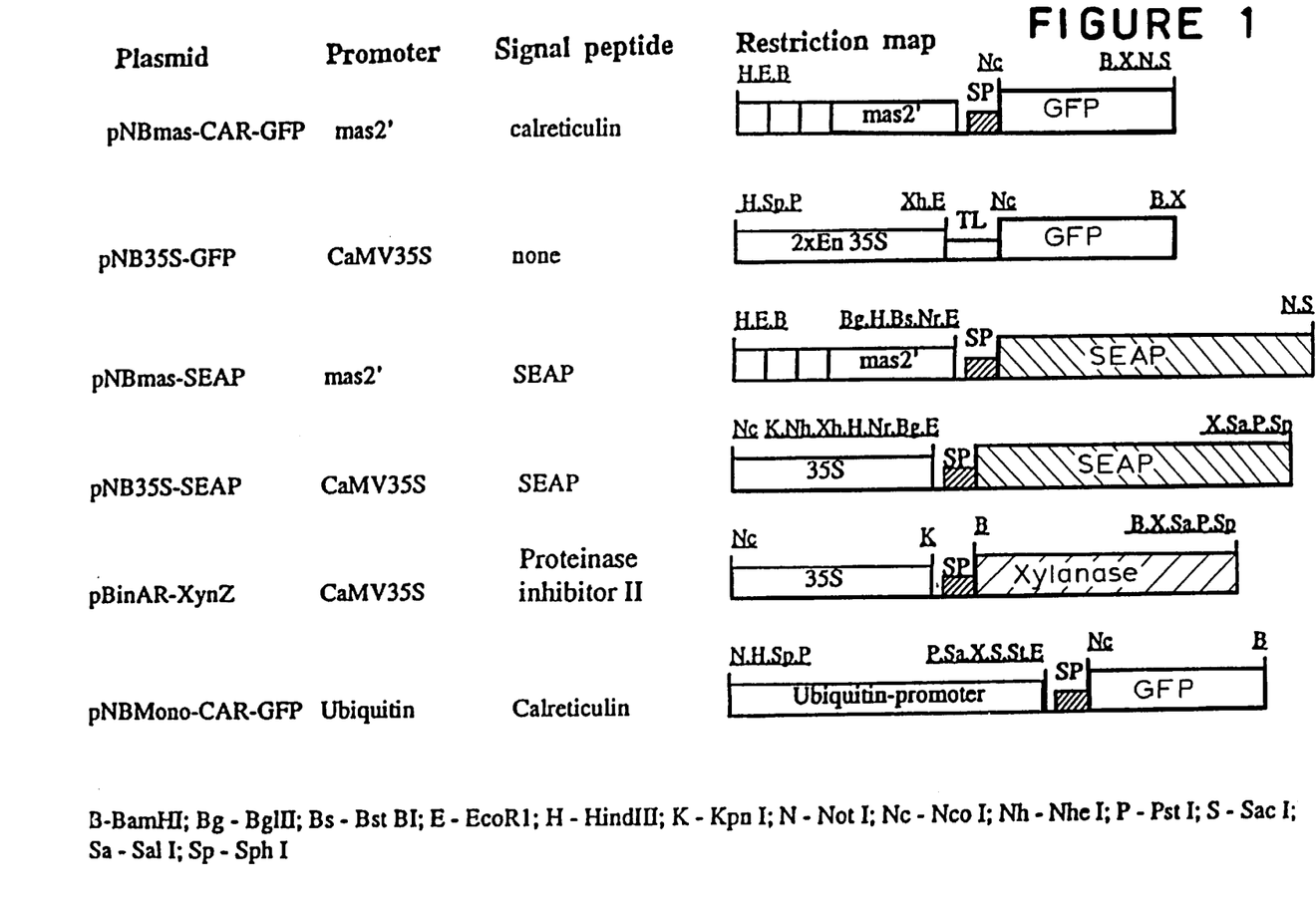
FIGS. 1–6 schematically illustrate relevant portions of the DNA molecules used in methods according to the invention.

Plasmid constructs designed for use in methods according to the invention are schematically illustrated in FIG. 1, wherein "Plasmid" indicates plasmid identities; "Promoter" identifies particular promoters (i.e., mas2' is the mannopine synthase promoter; 2xEn35S is the Cauliflower Mosaic Virus 35S promoter with two enhancers; 35S is the Cauliflower Mosaic Virus 35S promoter; and Ubiquitin is the Maize Ubiquitin promoter); "Signal peptide" identifies the signal peptides encoded by the plasmids; and Restriction map provides schematic physical maps of the plasmids indicating coding regions and expression elements (i.e., TL-the TEV 5' nontranslated sequence; SP is a coding region for the relevant signal peptide; GFP is Green Fluorescent Protein, SEAP is Human Placental Secreted Alkaline Phosphatase, and Xylanase is the enzyme from *Clostridium thermocellum*). Restriction sites are indicated as follows: B-BamHI, Bg-Bg/II, Bs-Bst/BI, E-EcoRI, H-HindIII, K-KpnI, -NotI, Nc-NcoI, Nh-NheI, P-PstI, S-SacI, Sa-SalI, Sp-SphI.

Figure 2:
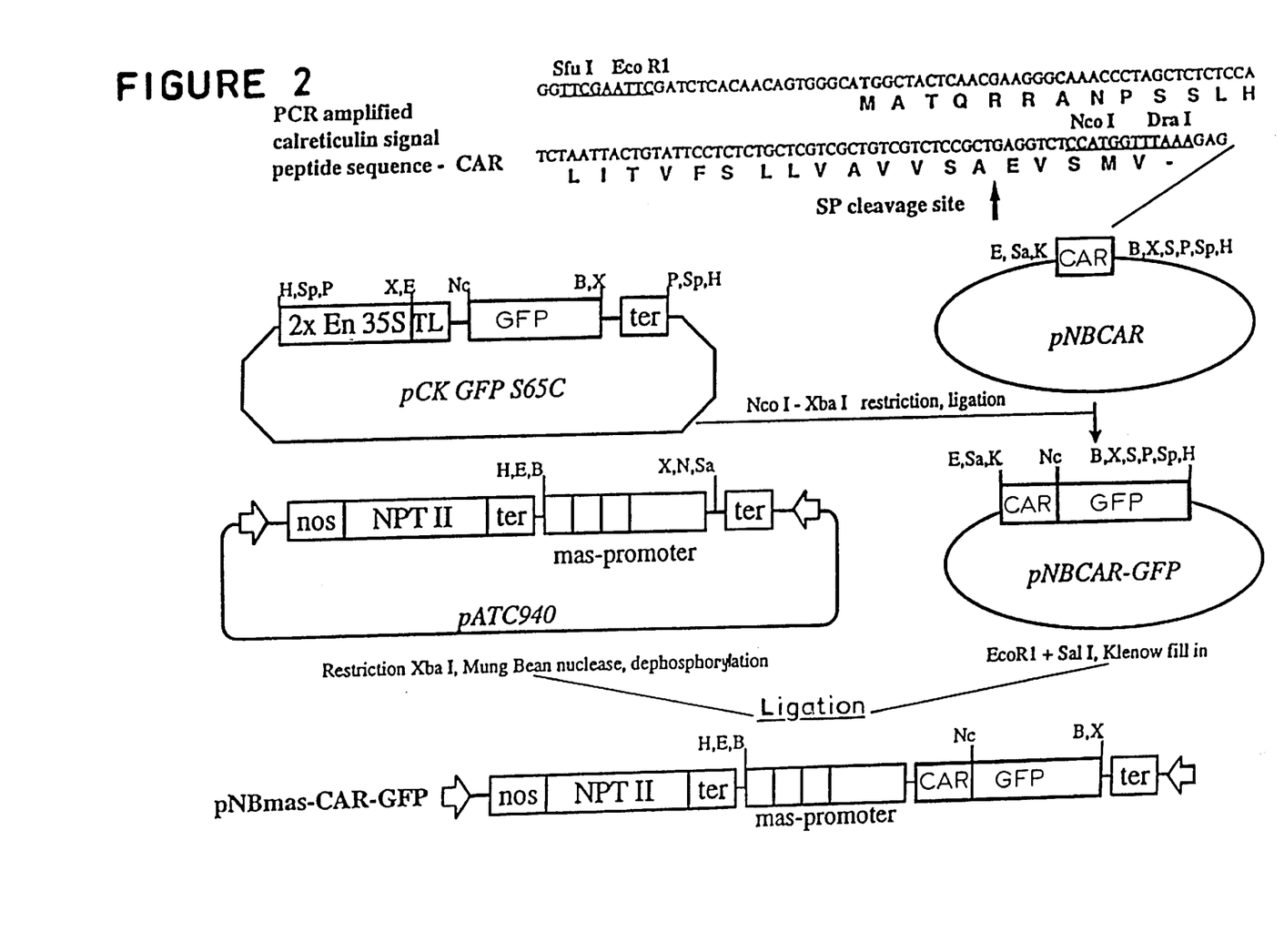

The plasmid pNBmas-CAR-GFP was used to recombinantly express GFP under the control of mas2' (Ni et al., Plant Mol. Biol. 30:77–96 (1996)), a mannopine synthase promoter exhibiting a strong preference for expression in roots (i.e., a root-preferential promoter). Construction of pNBmas-CAR-GFP proceeded in several steps, as illustrated in FIG. 2, starting from the pUC-based plasmid pCK GFP S65C containing a modified GFP coding sequence, as described in Heim et al., Nature 373:663–664 (1995). The modification, a change in codon 65 resulting in a substitution of Cysteine for Serine (S65C), resulted in a six-fold increase in the intensity of green fluorescence, as reported by Reichel et al. Proc. Natl. Acad. Sci. (USA) 93:5888–5893 (1996).

To direct GFP into the secretory pathway, the GFP coding region was fused to the coding region for a tobacco signal peptide, to wit, the endoplasmic reticulum resident protein Calreticulin. A cDNA fragment coding for the Calreticulin N-terminal signal peptide of 27 amino acids, along with the upstream 21 bp 5'-untranslated sequence, was amplified by PCR using forward Clamp1b: 5'-GGTTCGAATTCGAT-CTCACAACAGTGGGCATGG-3' (SEQ ID NO. 1) and reverse Clamprev: -5'CTCTTTAAACCATGGAGA-CCTCAGCGGAGACGAC-3' (SEQ ID NO. 2) primers and the plasmid Cal1-Np1 containing the full-length Calreticulin cDNA (Genbank Accession No. Z71395) as an amplification template. The amplified fragment contained the Calreticulin (CAR) signal peptide coding region flanked by restriction sites SfuI and EcoRI at the 5' terminus, and NcoI and DraI sites at the 3' terminus. The forward primer Clamp1b was designed such that the NcoI site (5'-CCATGG-3'), located in the 5'-untranslated region of Cal1-Np1, was destroyed by replacing the 5' "C" with a "G." The reverse primer was designed to place an NcoI site in the Calreticulin signal peptide coding sequence at a position two codons downstream from the encoded signal peptide (SP) cleavage site, thereby creating an NcoI site useful in fusing the Calreticulin signal peptide coding region to a heterologous polypeptide coding region, such as the GFP coding region. At positions −9 to −12 of the 5' untranslated region of Calreticulin mRNA is an AACA sequence for efficient translation initiation in plants.

As indicated in FIG. 2, a PCR amplified DNA fragment encoding the Calreticulin signal peptide was cloned into dephosphorylated pUC 18 at the SmaI site using the Sure-Clone Ligation kit (Pharmacia, Inc.) to generate the plasmid pNBCAR. The Calreticulin signal peptide-GFP fusion was carried out by cloning the NcoI-XbaI fragment of plasmid pCK GFP S65C into the NcoI and XbaI sites of pNBCAR to generate pNBCAR-GFP. The fusion point was confirmed by sequence analysis of pNBCAR-GFP. To place the CAR-GFP fused coding region under the control of the mas2' promoter, pNBCAR-GFP was digested with EcoRI and SalI and the fragment containing the fused coding re-ion was isolated following, agarose gel electrophoresis. This fragment was then rendered blunt-ended by a standard fill-in reaction with deoxynucleoside triphosphates and the Klenow fragment of DNA polymerase I. Plasmid pATC940 was used as a source for the mannopine synthase promoter, mas2'. Plasmid pATC940 contains, in the 5'-3' orientation, the selectable marker expression cassette (nos promoter, NPTII, and a terminator sequence), the mas2' promoter, a unique XbaI site, and a terminator. This plasmid was digested with XbaI, followed by Mung Bean nuclease digestion to blunt the ends of the linearized pATC940. The DNA fragment containing CAR-GFP was then inserted into the linearized pATC940 to generate pNBmas-CAR-GFP. Proceeding in the 5'-3' direction, pNBmas-CAR-GFP contains the selectable marker, the mas2' promoter, the CAR signal peptide coding region, the GFP coding region, and a terminator for the GFP expression unit.

Figure 3:
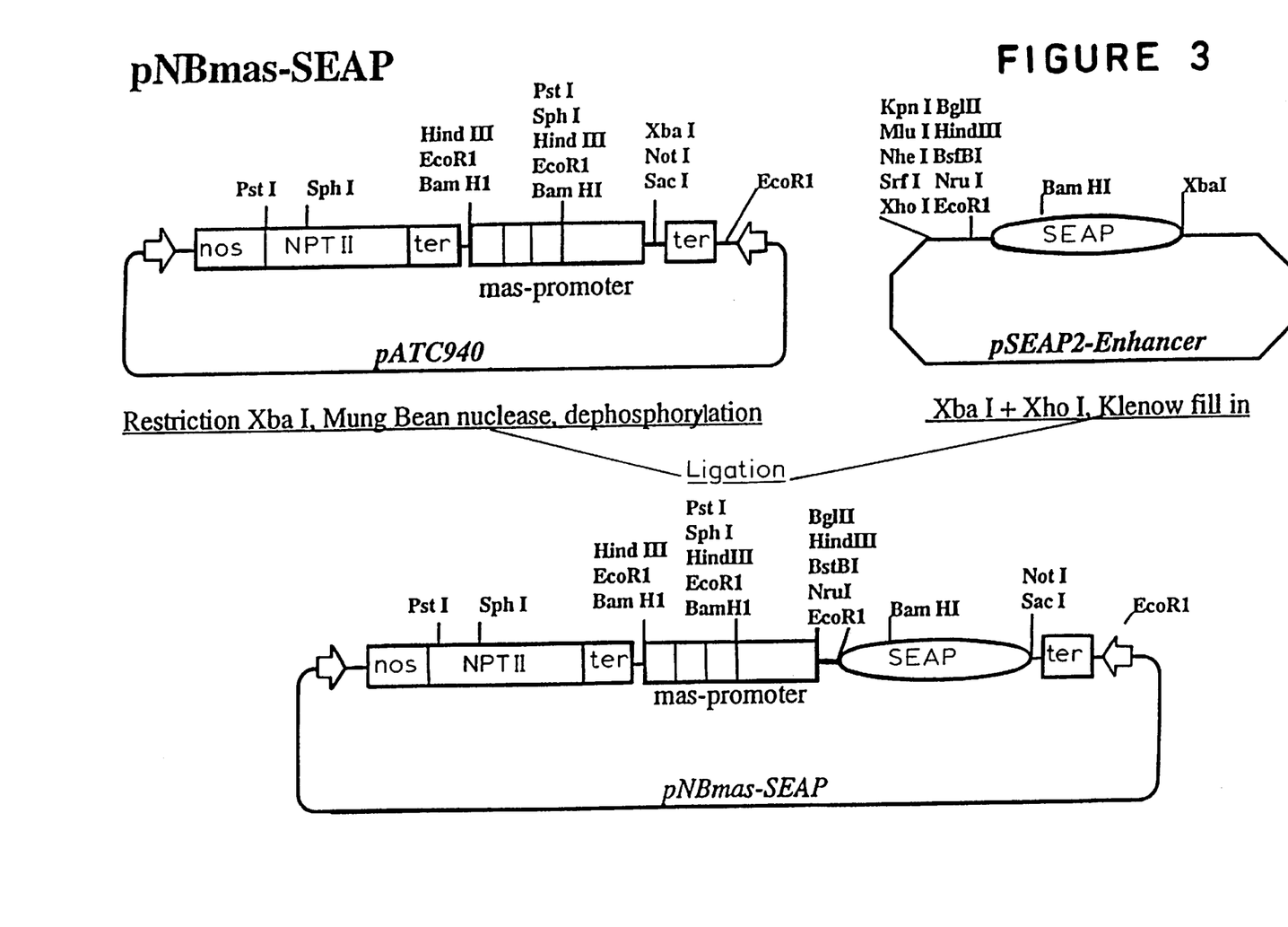

Recombinant expression of SEAP was also directed by the mas2' mannopine synthase promoter. The plasmid used for this expression, pNBmas-SEAP, was constructed by inserting the SEAP coding region into the plasmid pATC940, as schematically shown in FIG. 3. The SEAP coding region was excised from the pSEAP2-Enhancer plasmid using XhoI and XbaI. Again, the overhanging ends were filled using Klenow and the standard deoxynucleoside triphosphates. The vector pATC940 was prepared by restriction with XbaI, Mung Bean exonucleolytic digestion, and dephosphorylation. Insertion of the fragment containing the SEAP coding region into the blunted XbaI site of pATC940 generated pNBmas-SEAP, which was used in practicing the methods of the invention.

The Cauliflower Mosaic Virus promoter CaMV 35S was used to independently direct the recombinant expression of SEAP, GFP and Xylanase in plant cells.

Figure 4:
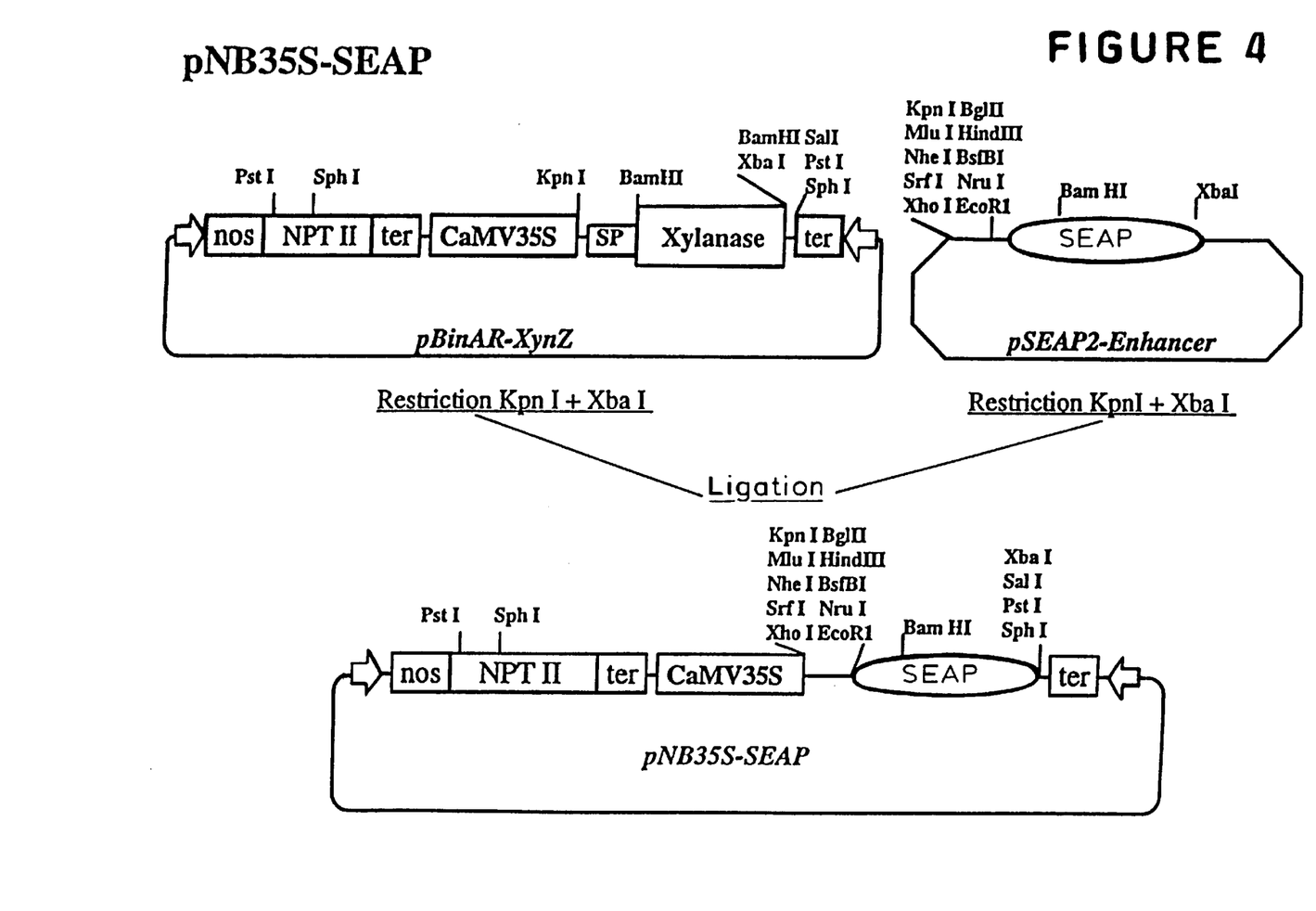

SEAP was expressed under the control of the CaMV 35S promoter using the plasmid pNB35S-SEAP. The SEAP coding region (encoding the 492 amino acid SEAP protein), along with the coding region for a signal peptide ($H_2N$-MLLLLLLLGLRLQLSLG) (SEQ ID NO. 3), was excised from the pSEAP2-Enhancer plasmid (Great EscAPe System; Clontech, Inc.) with KpnI and XbaI. This fragment was then cloned into KpnI-XbaI-digested plant transformation vector pBinAR-XynZ, as described by Herbers et al., Bio/Technology 13:63–66 (1995). This vector contains, in the 5'–3' orientation, the above-described NPTII selectable marker expression cassette, the CaMV 35S promoter, a unique KpnI site, a signal peptide coding region (i.e., the N-terminal portion of the potato-derived vacuolar Proteinase Inhibitor II; see, von Schaewen et al., EMBO J. 9:3033–3044 (1990)), the Xylanase coding region, a unique XbaI site, and the OCS (i.e., Octopine Synthase) terminator, as shown in FIG. 4. Digestion of pBinAR-XynZ with KpnI and XbaI released the fragment bearing the signal peptide sequence and the Xylanase coding region. The released fragment was replaced by a KpnI-XbaI fragment bearing the coding region for SEAP (the SEAP Signal Peptide fused to the mature SEAP protein) from the pSEAP2-Enhancer plasmid, thereby generating pNB35S-SEAP (FIG. 4). The resulting plasmid contained the signal peptide-SEAP fused coding region between the plant constitutive CaMV 35S promoter and the OCS-terminator.

Figure 5:
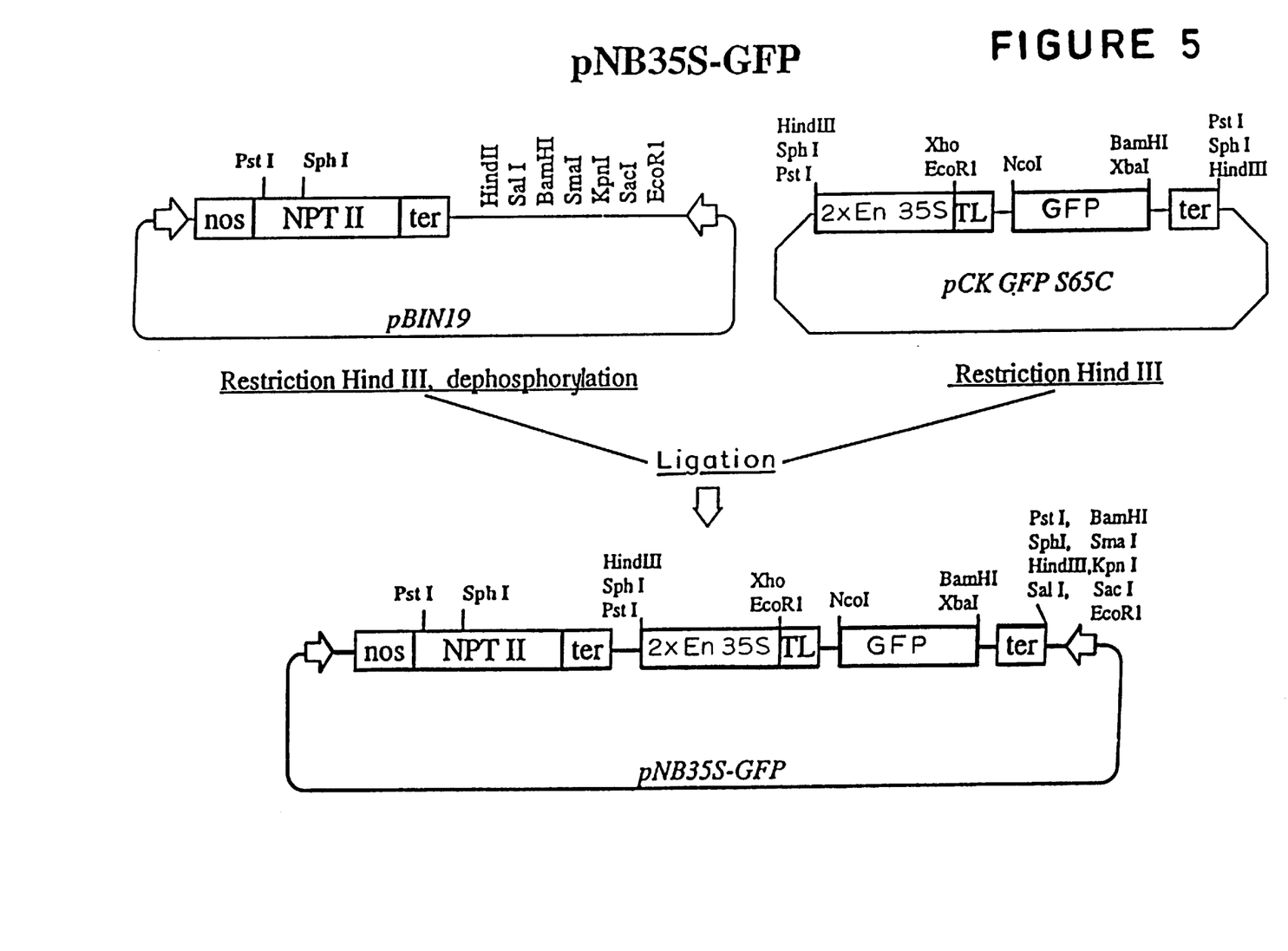
Figure 6:
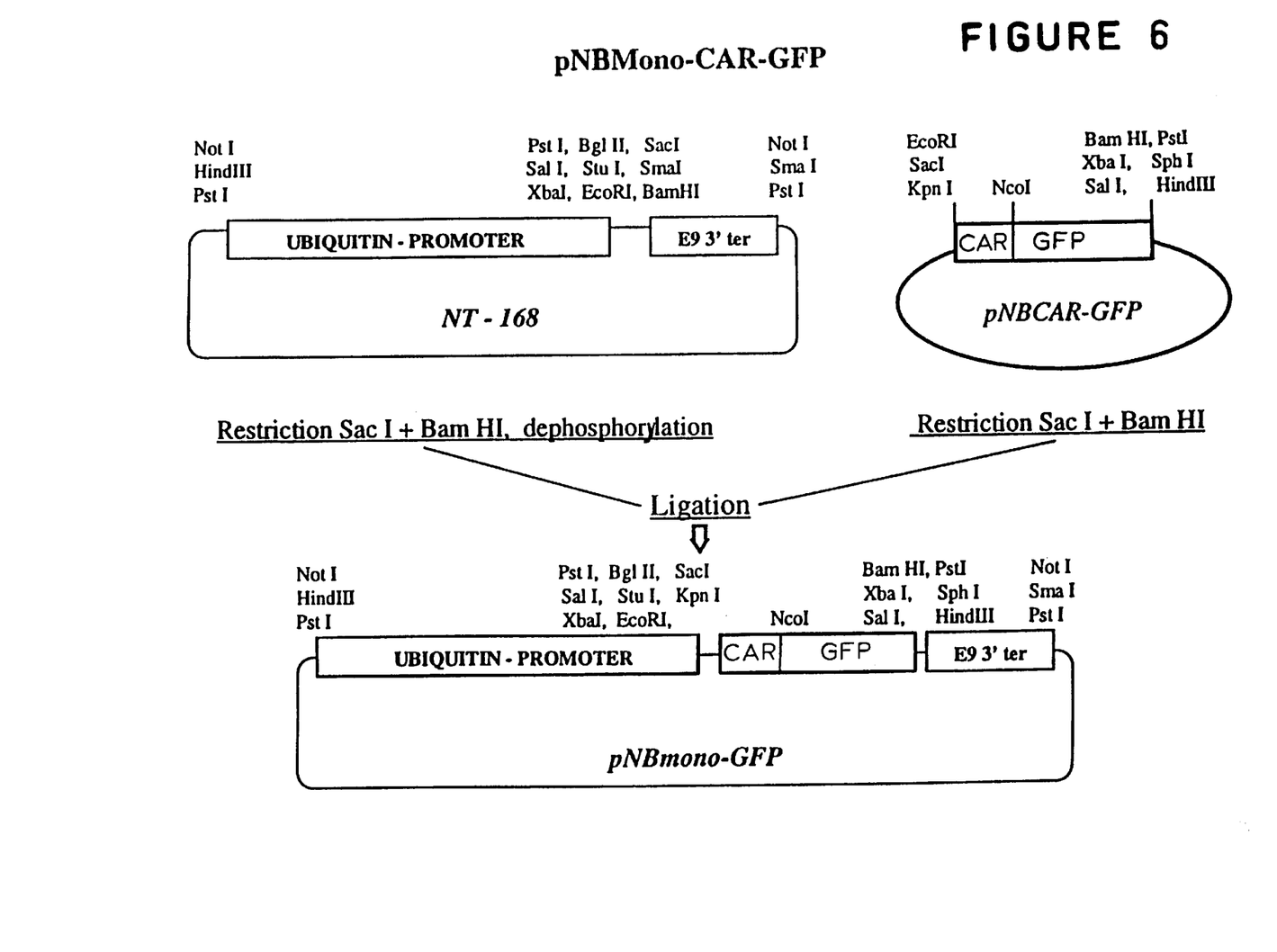

One plasmid used to express GFP from the CaMV 35S promoter was pNB35S-GFP. (See FIG. 5. This plasmid was constructed by initially restricting pCK GFP S65C with HindIII, thereby excising a fragment containing the GFP coding region flanked, in proper orientation, by the CaMV 35S promoter (including two enhancer sequences and a TEV 5' nontranslated sequence (TL)) and a terminator sequence. The vector pBin19, containing the previously described NPTII selectable marker expression cassette, was digested with HindIII and the GFP-containing fragment was inserted, thereby generating pNB35S-GFP (FIG. 5). GFP may also be expressed under the control of the Maize Ubiquitin promoter using plasmid pNBmono-GFP. The construction of pNBmono-GFP is shown schematically in FIG. 6. Initially, a DNA fragment encoding the Calreticulin signal peptide and GFP is excised from pNBCAR-GFP with BamHI and SacI and ligated into the BamHI site of plasmid Nt-68, thereby placing these fused coding regions between the monocot-specific Maize Ubiquitin promoter and a monocot terminator designated E9 3', as illustrated in FIG. 6.

Xylanase expression was also placed under the control of the CaMV 35S promoter functional in plant cells. Construction of PbinAR-XynZ, containing the Xylanase coding region of *Clostridium thermocellum* under the control of the CaMV 35S promoter, is described in Herbers et al, 1995, and is graphically illustrated in FIG. 4.

The invention contemplates methods involving plasmids, including the plasmids described above. Additionally, other means for introducing the coding regions of heterologous polypeptides into plants are contemplated by the invention. Viruses, bacterial genomes, plasmids, phagemids, cosmids, and other vectors may be employed as long as they are functional in delivering the coding region of interest to the desired cells. Preferred vectors include expression control signals that permit a measure of control in expressing a heterologous polypeptide. Also preferred are vectors that encode a selectable marker to facilitate identification of recombinant plant cells. The invention also embraces non-vector-based methods for introducing the coding regions of heterologous polypeptides, e.g., ballistic methods for polynucleotide introduction and transformation of plant cell protoplasts with polynucleotides that may be either transiently expressed or integrated into a resident polynucleotide and expressed.

EXAMPLE 2

Generation of Transgenic Plants

The recombinant polynucleotides described in Example 1 were separately introduced into plants using *Agrobacterium tumefaciens*. The streptomycin-resistant *Agrobacterium tumefaciens*, strain LBA4404 was transformed with recombinant polynucleotides using the freeze-thaw procedure described by Hood et al., J. Bacteriol. 168: 1291–1301 (1986). Transformation of *Agrobacterium tumefaciens* LBA4404 was confirmed by Southern DNA hybridization. Although pBin19 (a plant transformation vector) and *A. tumefaciens* LBA4404 are preferred for use in practicing the present invention, any of the conventionally known and available plant transformation vectors and *A. tumefaciens* strains may be used.

Transformation of tobacco plants (e.g., Nicotiana tabacum cv. Wisconsin and cv. Samsun NN) was effected by leaf-disk co-cultivation, as described by Weissbach et al., in Plant Molecular Biology-Technique (Academic Press, Inc. 1988). Healthy unblemished leaves were harvested from sterile young plants and cut into strips 5–10 mm wide. These explant tissues were infected by submersion in a suspension of Agrobacterium cells transformed with an appropriate binary vector such as described in Example 1 (e.g., pBinAR-Xynz) that had been grown at 28° C. for 40–48 hours in liquid YM medium containing streptomycin and kanamycin, each at 50 mg/L. One liter of YM medium contains 0.4 g yeast extract (autolyzed, low sodium); 10 g mannitol; 0.1 g NaCl; 0.2 g $MgSO_4$ and 0.5 g of $K_2HPO_4$. YM medium (Gibco BRL) is specifically formulated for the growth and expression of Agrobacterium. Explant tissues were then blotted dry on sterile filter paper, inverted, and placed on MS medium in tissue culture plates and incubated for a co-cultivation period of 36–48 hours. (MS medium is a conventional medium for the in vitro culture of plants. Murashige et al., Plant Physiol. 15:473–497 (1962).) Subsequently, explants were transferred to agar plates (8 g/L) containing regeneration medium (MS salts, 30 g/L sucrose, 1 mg/L BAP (i.e., 6-benzylaminopurine, a plant cytokinin), 500 mg/L of carbenicillin to eliminate bacterial growth, and 100 mg/L of kanamycin as a selective agent for transgenic plants). Transformants were selected on the same medium without any hormone. Incubation was continued until roots had formed.

Beyond the traditional use of Agrobacterium-based transformation protocols to transform dicots, continued efforts have shown that Agrobacterium-based methods may also be employed to transfer heterologous (i.e., non-native) nucleic acids to monocot species in the generation of transgenic plants for use in methods according to the invention. Smith et al., Crop Science 2: 301–309 (1995), incorporated herein by reference.

Other transformation methodologies may also be employed to generate transgenic plants, as would be understood in the art. For example, direct DNA transfer into plant cell protoplasts may be effected by the conventional techniques of calcium phosphate co-precipitation, the use of poly-L-ornithine, liposome-mediated transformation, electroporation, microinjection or fusagen-mediated (e.g., polyethylene glycol) transformation, and plants regenerated from the transformed protoplasts. PCT/US84/00050 and Christou, Euphytica 85: 13–27 (1995), each incorporated herein by reference. Other transfer methodologies such as biolistic transformation (i.e., microprojectile or particle bombardment) do not require plant cell protoplasts, thereby simplifying the process of regenerating transgenic plants. Consequently, biolistic transformation may be employed to introduce the coding region for a heterologous polypeptide into a wide variety of plants, including both monocots and dicots. Christou (1995); Jahne et al., Euphytica 85:35–44 (1995), incorporated herein by reference.

Regeneration of transgenic plants from transformed cells, including transformed protoplasts, may nevertheless be accomplished using any one of several techniques known in the art. Several approaches to the regeneration of transgenic plants are disclosed in EP-A-0 243 553, incorporated herein by reference. These approaches include regeneration via embryogenic or organogenic routes. Alternatively, plants may be regenerated following transformation by a method that incorporates a step for inducing meristem reorganization to improve the chances of transgenic cells contributing to the germline, followed by a step providing conditions promoting differentiation of meristem. PCT/US95/08977, incorporated herein by reference. In general, any of the transformation and regeneration methodologies known in the art may be used to generate transgenic plants for use in methods according to the invention.

EXAMPLE 3

Production and Recovery of Xylanase using Transgenic Tobacco Plants

Following root formation, hydroponic cultivation was initiated by placing the transgenic plants into sterile liquid MS medium containing 15 g/L of sucrose, 500 mg/L cefotaxime and 100 mg/L of kanamycin. Wild-type control plants (i.e., untransformed plants) were cultivated in a similar medium without antibiotics. Plants were positioned in a synthetic stopper to permit the roots to contact the medium under sterile conditions while the remainder of the plants (i.e., plant regions above the hypocotyl under normal gravimetric culture conditions) were in an open and non-sterile environment.

Beginning approximately 2–3 weeks after rooting, exudates were periodically sampled by aspiration of medium with sterile syringes. The protein content of intercellular fluids was also examined. Intercellular fluids were isolated as described by Parent et al., Can. J. Bot. 62:564 (1984) with some modifications. After washing with water, freshly harvested roots or leaves were infiltrated with an appropriate ice-cold buffer (50 mM Na-acetate buffer, pH 5.9) under vacuum. Infiltrated tissues were centrifuged at 350×g for 15 minutes to isolate the intercellular fluid. Intercellular proteins were concentrated by ultrafiltration (Microcon 10 membranes having a 10 kD cut-off, Amicon, Inc.). Samples were incubated at 65° C. for 30 minutes to denature thermolabile proteins (GFP, SEAP and Xylanase are heat stable), rapidly cooled on ice, and stored at −20° C.

Xylanase assays were performed essentially as described by Biely et al., Methods Enzymol. 160:536–542 (1988). In brief, RBB-xylan (11.5 mg/ml Sigma Chemical Co.) was incubated at 60° C. for 20 minutes with protein extract in a final volume of 240 µl 50 mM sodium acetate (NaOAc), pH 5.4. The reaction was stopped by adding 480 µl of 96% ethanol. After standing at room temperature for 30 minutes, the precipitate was removed by centrifugation for 3 minutes at 15,000×g. The smaller blue-stained fragments found in the supernatant indicated Xylanase activity. A total of 50 individual transformants were analyzed and 35 of them showed Xylanase activity in both root exudates and intercellular fluids.

Detection of Xylanase by native polyacrylamide gel electrophoresis (PAGE) was carried out according to Biely et al. (1988). Native gels with fractionated proteins were layered over an agar-RBB-xylan gel preheated to 35–40° C. and incubated at room temperature until products were clearly visible. The agar layer was then removed from the separation gel and dipped into ethanol-0.05 M acetate buffer (2:1, pH 5.4). Xylanase activity was detected as an increase in the rate of diffusion of dyed fragments resulting from polysaccharide hydrolysis.

Visualization of exuded Xylanase from roots was performed by growing transgenic plants on agar medium containing RBB-xylan. Tobacco seeds were germinated on the agar medium containing 2.5 mg/ml of RBB-xylan and the growth of roots was visually monitored for 30 days. Clear zones around the roots of transgenic plants were formed as a result of exuded Xylanase activity. Sethu et al., Phytochemistry, 42: 961–966 (1996).

Quantification of exoxylanase activity was performed using the reducing sugar equivalent method described by Grepinet, et al., J. Bacteriol. 170:4582–4588 (1988). In brief, root exudates of wild-type (control) and transgenic plants were heat-treated for 20 minutes at 65° C., and concentrated 10-fold by ultrafiltration. A 300 µl aliquot of each sample was added to 0.2 ml of 0. 15% w/v xylan (Birchwood, Sigma Chemical Co.) prepared in 100 mM NaOAc (pH 5.4), and the mixture was incubated at 37° C. in a thermostatic shaker. After 30 minutes, the incubation reaction was stopped by rapid cooling to room temperature, followed by the addition of 0.6 ml of dinitrosalicylic reagent. Glucose was used to prepare standard curves. Duplicate control reactions were stopped prior to any incubation. Samples were boiled 10 minutes and the adsorbance at 500 nm was determined spectrophotometrically. Enzyme activity was assayed using equivalent concentrations of xylose. One unit of Xylanase activity was defined as that quantity of enzyme that catalyzed the formation of 1 micromole of reducing group per minute (Achmed et al., Plant Physiol. 65: 11014–1016 (1980)). Transgenic plants produced a total secreted Xylanase activity of 3.6 units from 960 mg of roots (wet weight); wild-type plants exhibited a background level of Xylanase activity (i.e., <0.1 units of secreted Xylanase activity from 1,300 mg of roots) using this assay. Specific Xylanase activity was 3.8 units/gFW for transgenic plants and less than 0.01 units/gFW for wild-type controls. In terms of protein quantities equivalent to these activity levels, transgenic plants produced approximately 20 ing of Xylanase while wild-type plants produced less than 0.1 mg of the protein. (Purified Xylanase from *Trichoderma virdis* has a specific activity of 182 U/mg of protein (Sigma Chemical Co.))

A wide variety of plants may be used in the methods according to the invention.

Exudates produced by e.g., roots, leaves, etc. may be used in practicing the invention. Having been externalized by the plant or plant portion, exudates are readily obtained by any conventional method, including intermittent or continuous bathing of the plant portion (whether isolated or part of an intact plant) with fluids. Preferably, exudates are obtained by contacting the plant or plant portion with an aqueous solution such as a growth medium or water. The fluid-exudate admixture may then be subjected to conventional polypeptide purification techniques to isolate the desired polypeptide.

EXAMPLE 4

Production and Recovery of SEAP using Transgenic Tobacco Plants

Transformation of tobacco plants (line SN-27) to introduce the human Secreted Alkaline Phosphatase (SEAP) coding region under the control of either the CaMV 35S promoter or the root-preferential mas2' promoter were performed as described in Examples 1–2. Transgenic tobacco plants transformed with the human secreted alkaline phosphatase (SEAP) gene under the control of the CaMV 35S promoter were also rooted and aseptically cultivated in liquid medium for 33 days. Transgenic plants were tested for the presence of specific nRNAs by Northern hybridization, using the method of Chomczynski et al., Anal. Biochem. 162:156 (1987) to isolate total RNA from leaf and root tissues. Transformed plants showed expression of SEAP-specific mRNA. Plants transformed with the human SEAP gene under the control of the CaMV 35S promoter showed similar mRNA expression levels in both leaf and root tissues. In contrast, transgenic plants expressing SEAP from the mas2' promoter demonstrated higher mRNA expression levels in root tissue than in leaf tissue.

Recovery of protein for analysis was performed as described in Example 3. SEAP activity was determined in liquid medium following 33 days of root growth and the removal of the roots to recover SEAP, as well as in the intercellular fluids. The chemiluminescent substrate CSPD, provided in the Great EscAPe SEAP Chemiluminescence Detection kit (Clontech, Inc.), was used to monitor the expression of SEAP by measuring secreted phosphatase activity. Chemiluminescent detection of SEAP activity was performed using either a Turner TD-20e Luminometer or by exposing the 96-well microtiter plates, where reactions were performed, to X-ray film.

The assay was performed with 25 µl samples of either intercellular fluid or root exudates. These samples were placed into 75 µl of proprietary dilution buffer (Clontech, Inc.) and incubated for 30 minutes at 65° C. to inactivate endogenous phosphatase activity. Subsequently, samples were incubated for 10 minutes with CSPD and a chemiluminescence enhancer in a reaction buffer containing L-homoarginine as an inhibitor of endogenous phosphatases, as described by Cullen et al., Methods Enzymol. 216:362–368 (1992). Samples from untransformed tobacco plants provided negative controls, samples containing purified Placental Alkaline Phosphatase served as positive controls.

Phosphatase activity was monitored in 50 individual tobacco plants transformed with the SEAP gene under the control of either the CaMV 35S or the mas2' promoter. Transgenic plants expressing SEAP from either promoter showed enzymatic activity. No phosphatase activity was detected in wild-type plants.

Plants transformed with a CaMV 35S expression cassette demonstrated stable SEAP activity in root exudates as well as in the leaf and root intercellular fluids. Total protein was found to increase linearly to a final concentration of approximately 1.4 mg/root (400 mg average root fresh weight at day 33). Production of SEAP during this period exhibited a 10-day lag and then accumulated linearly to a final concentration of approximately 0.11 mg/root. The distribution of total soluble protein and SEAP in the 33-day tobacco plants was also determined. Total soluble protein in root extract was approximately 65 mg/g of fresh root; 4.0% of that weight was SEAP. In the intercellular fluid, approximately 2 mg of total soluble protein was found in each gram of fresh root; SEAP represented 1.6% of this amount. In root exudate obtained from the aqueous medium in contact with the growing plants, total soluble protein was approximately 270 mg/g fresh root; 7.5% of that protein was attributable to the SEAP. In terms of the distribution of recombinant SEAP in these plants, 20.9% of the protein was found in the root extract, 0.29% in the intercellular fluid, and the vast majority, 78.8%, was found in the root exudate.

In contrast to the distribution of SEAP expressed using the CaMV 35S promoter, expression of SEAP under the control of the mas2' promoter was found predominantly in root samples, with less activity found in leaf samples. The results are presented in Table I below.

TABLE I

Quantification of the human secreted alkaline phosphatase (SEAP) in root exudates of transgenic tobacco plants

| Samples | Total soluble protein in the root exudates (µg) | Amount of SEAP in total secreted protein (%) | SEAP secreted per root (µg/gDW) | Activity of secreted SEAP per root U/gDW) |
|---|---|---|---|---|
| Line-32 | 1577 | 3.7 | 380 | 5.7 |
| Wild type | 1030 | not detected | not detected | not detected |

Thus, a recombinantly expressed protein (SEAP) was recovered from the exudate of transgenic tobacco plants without injury to the plants or expensive and cumbersome purification protocols to isolate the desired product.

The invention contemplates methods including a wide variety of sexually or vegetatively propagated plants, as well as intact living plant portions such as excised leaves, stems, roots, flowers, etc. Preferred for use in the methods of the invention are plant species representing different plant families such as tobacco, tomato, rapeseed, alfalfa and turfgrass. Other preferred plants are aquatic plants capable of vegetative multiplication, such as Lemna and other duckweeds, Azolla, floating rice, water hyacinth, and the flowering plants that grow submerged in water, such as eelgrass and wilgeon grass.

The plant or plant portion which is subjected to the process of the present invention is a living plant or plant portion which is intact, and which is capable of being sustained without the use of organic nutritional supplements and without maintaining sterile conditions for the plant. However, sterile conditions or inorganic supplements may be employed in the methods of the invention.

The plant which is used in the present invention may be a mature plant, an immature plant such as a seedling, or a plant germinating from a seed. Seeds may be germinated in natural waters or (germinated in prepared solutions or open fermenters. As noted above, a plant portion may also be used. Preferred plant portions are capable of being sustained without organic nutrient supplementation and do not require sterile conditions.

The plants or plant portions for use in the methods of the invention may be genetically modified by, e.g., transformation with wild-type or recombinant *Agrobacterium tumefaciens*. In general, the plants or plant portions may exhibit a genotype that differs from the genotypes of any naturally existing plants. Moreover, the genetic modification may be achieved by any one of the conventional methods for altering the genetic content of cells, as is understood in the art. Typical genetic modifications would involve the introduction of a heterologous coding region, the introduction, rearrangement or modification of one or more expression control sequences, the modification of the genetic elements involved in secretion/exudation, or the alteration of genetically controlled regulatory mechanisms.

One of ordinary skill in the art will also appreciate that the methods of the invention do not necessarily destroy the plants or plant portions. Accordingly, the methods may be either continuous or batch-mode processes.

EXAMPLE 5

Production and Recovery of GFP using Transgenic Tobacco Plants

Transformation of plants, hydroponic cultivation, and sample collection were performed as described in Examples 1 and 2. Transgenic GFP plants were tested for the presence of specific mRNAs by Northern hybridization. Total RNA was isolated from leaf and root tissues using the procedure of Chomczynski et al., (1987). All transformed plants expressed GFP-specific mRNA.

The unique bioluminescent features of GFP (excitation at 475 nm, emission at 510 nm) were used to microscopically detect and localize this protein in plant tissues and liquid samples. Plant roots freshly prepared in 0.05 M Tris-HCl, pH 8.0, were irradiated in the long-UV range of the electromagnetic spectrum with a fluorescent microscope (Nikon, Inc.). Transgenic roots were exposed to UV for an empirically optimized period of 30 seconds, which maximized the distinction between the brightly fluorescing roots of transgenic plants and the non-fluorescing roots of wild-type plants.

To investigate the possibility of secreted and exuded GFP, intercellular fluid and culture media were exposed to DEAE-Sephacel anion-exchange beads (Sigma Chemical Co.) to immobilize proteins. Anion-exchange beads incubated with the intercellular fluid or exudates of control plants were pale yellow under the fluorescent microscope, while beads exposed to the apoplastic fluid or root cultivation medium of GFP transformants exhibited a bright green fluorescence, indicating the presence of secreted GFP.

Immunological detection of GFP was performed by Western blotting using anti-GFP monoclonal antibodies produced by mouse hybridoma cells (Clontech, Inc.) using the Western Exposure Chemiluminescent Detection System PT 1600-1, available from the same supplier. Proteins isolated from the root exudates and root intercellular fluid were separated on 12% PAGE and electophoretically transferred onto PVDF membranes using the Bio-Rad Mini-Protein system (100 V constant voltage at 4° C., 1.5 h). Pre-stained low-molecular weight SDS-PAGE standards (Bio-Rad Laboratories, Inc.) were used as molecular weight markers. Primary antibodies were diluted 1:500 and the secondary antibody-alkaline phosphatase conjugate was diluted 1:15, 000. A single sharp band corresponding to a 27 kDa protein was detected in protein samples of root exudates and root intercellular fluid of transgenic plants. No specific signals were detected in the corresponding samples of wild type plants.

EXAMPLE 6

Production and Recovery of HbsAgS and HbsAgM using Transgenic Plants

Hepatitis B virus (HBV) is the human member of the hepadnaviradae family of viruses which infects over 300 million people worldwide. The HBV genome encodes three related envelope proteins termed L, M, and S. The three proteins are produced from a single open reading frame through alternative translation start sites. All three proteins have a common N-linked glycosylation site specified by the S coding region, while the M protein alone contains an additional glycosylation site at amino acid position 4 of the pre-S2 domain. Recently, Mehta et al., Proc. Natl. Acad. Sci. (USA) 94:1822–1827 (1997) disclosed that glycosylation of M protein is critical for its secretion from animal cells.

For the production of hepatitis B surface antigen, the S-protein coding region and the M-protein coding region are independently fused to a Calreticulin signal peptide coding region and placed into plant transformation vector pNB-CAR to generate pNB-CAR-HBsAgS and pNB-CAR-HBsAgM, respectively. DNA fragments encoding the S and M proteins are amplified by PCR using specific primers and pHB320 as a template, as described by Bichko et al., FEBS Lett. 185:208–212 (1985). This plasmid, pHB320, contains the complete genome of the ayw subtype of Hepatitis B.

Transformation and analysis of the transformed plants are performed as described in Examples 1 and 2. Proteins exuded from the roots (i.e., root exudate) or leaves (i.e., guttation fluid exuded from hydathodes) of transgenic plants are analyzed using commercially available antibodies against HBV surface proteins.

EXAMPLE 7

Production and Recovery of Heterologous Polypeptides using Transgenic Tomato Plants Plasmids pNBmas-CAR-GFP and pNBmas-SEAP, encoding GFP and SEAP as reporters, respectively, are used to transform tomato plants (variety Dinasty). Tomato transformation is performed using a modification of the leaf-disk and *A. tumefaciens* co-cultivation protocol described in Example 2. The protocol is modified by using an *A. tumefaciens* titer of about $10^7$ cells/mil, which will have been grown overnight in liquid LB medium. For nurse plates, MS salts are reduced to 10% of their normal concentration, as described by Weissbach, 1988, using a suspension culture of *N. tabacum* as the nurse culture. The *N. tabacum* cells are grown in liquid medium containing MS salts, $B_5$ vitamins, sucrose (30 g/L) and p-chlorophenoxyacetic acid (2 mg/L). Nurse plates are prepared by adding a 1–1.5 ml aliquot of the *N. tabacum* culture to the plate and covering the aliquot with an 8.5 cm disk of Whatman No. 1 filter paper. Infected explants are placed on top of the filter paper and incubated. Selection and regeneration of transformants are performed on a selective medium supplied with 25–50 mg/A of kanamycin.

Analysis of the transformed plants is performed as described above, and the heterologous polypeptides are recovered from, e.g., root and leaf exudates, also as described above.

EXAMPLE 8

Production and Recovery of Heterologous Polypeptides using Transgenic Turfgrass Plasmid pNBCAR-GFP, containing the GFP coding sequence of pCK GFP S65C (Reichel et al., (1996)), fused to the Calreticulin signal peptide, is used to construct a transformation vector for the expression of GFP in turfgrass, a monocot.

Transformation of turfgrass is carried out using a particle gun transformation method. See, Christoer, Euphytica 85:13–27 (1995) and Johne et al., Euphytica 85:35–44 (1995). Analysis of the transformants and polypeptide recovery are accomplished as described above.

EXAMPLE 9

Production and Recovery of Heterologous Polypeptides from Guttation Fluid using Transgenic Tomato Plants Plasi'ds pNBmas-CAR-GFP and pNBmas-SEAP, encoding GFP and SEAP as reporters, respectively, are used to independently transform tomato plants (variety Dinasty), as described in Examples 2 and 7. Transformed tomato plants are grown in soil which is covered by a water-impermeable barrier. An opening in the barrier allows the stems of the tomato plants to extend above the soil. Water is supplied to the soil by any conventional technique for introducing water that is compatible with the water-impermeable barrier, e.g., water may be pumped into the soil using, conventional piping or tubing. The leaf and stem portions of the tomato plants are contacted with an aqueous medium, which may be water, and the heterologous polypeptide is recovered in an admixture of aqueous medium and a plant exudate such as guttation fluid. The admixture may be collected from the surface of the water-impermeable barrier. The fluid is then subjected to conventional purification methodologies to recover the heterologous polypeptide.

In accordance with another aspect of the invention, the aqueous medium contacting step is omitted and undiluted plant exudate, e.g. guttation fluid, is recovered. In one embodiment, guttation fluid is passively collected on the barrier due to gravitational force. In other embodiments, active collection of the exudate is accomplished by mechanical agitation of the plant or a portion thereof Mechanical agitation serves to induce exudate movement, in the ultimate direction of the barrier, for example by flowing down the plant or portion thereof or by traveling through the air in the form of drips or mist. The agitator may be any conventional means for inducing exudate movement. Examples include a rod or a cable for making sufficient contact with a plant or portion thereof to effect its physical deflection, resulting in movement of the exudate. Of course, the agitation may directly contact the exudate, which is in contact with the plant or portion thereof In addition to mechanical agitators, the invention contemplates non-mechanical agitators such as pressurized gas, e.g. air, delivered from any conventional source such as an air compressor. In still other embodiments, the heterologous polypeptide-containing exudate is recovered using) a device that function as both agitators and collectors. For example, a water-impermeable implement may be brought into contact with the plant or portion thereof, e.g., by dragging the device across the plant or portion thereof The contact is sufficient to induce exudate movement and the device collects exudate separated from the plant or portion thereof Alternatively, absorbing or blotting devices (e.g., paper, cloth, etc.) are used to contact the plant or portion thereof bearing the heterologous polypeptide-containing exudate.

Any conventional technique for soil watering may be used in the method of the invention, including the use of gravity- or pump-driven water supply piping or tubing. Alternatively, the soil may contain any of the irrigation systems known in the art. In addition, the invention contemplates reliance on capillary action in passively supplying water to the soil from adjacent areas. Those of skill in the art will recognize that, in addition to soil-based methods for recovering heterologous polypeptide from exudates, the methods of the invention may be practiced using other forms of plant culture, such as hydroponics and aeroponics.

The water-impermeable barrier may be any substance suitable for preventing the passage of aqueous solutions without adulterating those solutions by releasing chemical constituents of the barrier. Preferably, the barrier can withstand typical environmental conditions of temperature, wind, etc. Also preferred are flexible barriers that are readily molded to existing or engineered soil contours.

The soil may be left in its natural topography or re-shaped to suit the methods of the invention. For example, the soil may be shaped into a collection of hillocks which, in combination with a flexible barrier, maximizes recovery of exuded polypeptide by directing the aqueous fluid containing an exudate away from any opening in the barrier provided to allow passage of a plant stein.

While the present invention has been described in terms of specific embodiments, it is understood that variations and modifications will occur to those skilled in the art. Accordingly, only such limitations as appear in the appended claims should be placed upon the invention.

What is claimed is:

1. In a process for recovery of a heterologous polypeptide from a plant having cells genetically transformed to express and secrete a heterologous polypeptide, the improvement comprising:

(a) externally contacting said plant, or an intact portion thereof wherein expression occurs, with an aqueous medium to effect an admixture of said medium and an exudate of said plant or said intact portion thereof; and (b) recovering said polypeptide from said admixture.

2. The process of claim 1 wherein said plant exudate is guttation fluid.

3. The process of claim 1 wherein said contacting step is performed in a culture system selected from the group consisting of hydroponics, aeroponics, and soil-based cultivation.

4. The process of claim 1 wherein said contacting and recovering steps are performed continuously.

5. The process of claim 1 wherein said plant or plant portion is selected from the group consisting of tobacco, tomato, rapeseed, ryegrass, alfalfa, turfgrass, eelgrass, wilgeon grass, duckweed, Azolla, floating rice, and water hyacinth.

6. In a process for recovery of a heterologous polypeptide from a plant having cells genetically transformed to express and secrete a heterologous polypeptide, the improvement comprising recovering said polypeptide from an exudate of said plant.

7. The process of claim 6 wherein said plant exudate is guttation fluid.

8. The process according to claim 6 wherein said heterologous polypeptide is expressed from a coding region introduced into said cells by a viral vector.

9. The process according to claim 1 wherein said heterologous polypeptide is expressed from a coding region introduced into said cells by a viral vector.

10. In a process for recovery of a heterologous polypeptide from a plant having cells containing a coding region for expression and secretion of a heterologous polypeptide, the improvement comprising:

(a) externally contacting said plant, or an intact portion thereof wherein expression occurs, with a medium to effect an admixture of said medium and an exudate of said plant or said intact portion thereof; and (b) recovering said polypeptide from said admixture.

11. The process according to claim 10 wherein a viral vector is used to introduce said coding region into the cells of said plant.

* * * * *